United States Patent [19]

Li

[11] Patent Number: 5,207,679
[45] Date of Patent: May 4, 1993

[54] SUTURE ANCHOR AND INSTALLATION TOOL

[75] Inventor: Lehmann K. Li, Wellesley, Mass.

[73] Assignee: Mitek Surgical Products, Inc., Norwood, Mass.

[21] Appl. No.: 902,513

[22] Filed: Jun. 22, 1992

Related U.S. Application Data

[63] Continuation of Ser. No. 766,025, Sep. 26, 1991, abandoned.

[51] Int. Cl.⁵ .............................................. A61B 17/00
[52] U.S. Cl. ........................................ 606/72; 606/75; 606/78; 606/232
[58] Field of Search ................... 606/72, 74, 75, 78, 606/139, 144

[56] References Cited

U.S. PATENT DOCUMENTS

| | | |
|---|---|---|
| 3,716,058 | 2/1973 | Tanner, Jr. . |
| 4,665,906 | 5/1985 | Jerris . |
| 4,721,103 | 1/1988 | Freeland ................ 606/86 |
| 4,738,255 | 4/1988 | Goble et al. ............ 606/86 |
| 4,898,156 | 2/1990 | Gatturna et al. ....... 606/232 |
| 4,899,743 | 2/1990 | Nicholson .............. 606/72 |
| 4,946,468 | 8/1990 | Li ............................ 606/232 |
| 4,968,315 | 11/1990 | Gatturna et al. ....... 606/232 |
| 5,002,550 | 3/1991 | Li ............................ 606/232 |
| 5,037,422 | 8/1991 | Haghurst et al. ....... 606/232 |
| 5,046,513 | 9/1991 | Gatturna et al. ....... 606/232 |

Primary Examiner—Stephen C. Pellegrino
Assistant Examiner—Gary Jackson
Attorney, Agent, or Firm—Pandiscio & Pandiscio

[57] ABSTRACT

A system for attaching an object to a workpiece including an anchor assembly and an installation tool is provided. The anchor assembly includes a body and at least two barbs. The body has a first portion having a first end, a reduced second portion having a second end and a middle portion connecting the first and second ends of the first and second portions respectively. The barbs extend from the first end of the first portion axially and radially outwardly to outer ends located radially outwardly of an axial projection of the maximum transverse cross-section of the first portion. Each barb is curved in its normal unstressed state, but is capable of being elastically deformed into longitudinal channels in the middle portion of the anchor assembly. The anchor assembly is deployed in a hole in the workpiece by an installation tool which is adapted to receive the reduced second portion of the anchor assembly in its distal end. The engagement of the second portion of the anchor assembly with the installation tool is re-enforced by axial projections from the distal end of the installation tool engaging indentations in the outer surface of the middle portion of the anchor assembly body. The method of installation includes the steps of mounting the anchor assembly to the distal end of the shaft of the tool, aligning the longitudinal axis of the shaft with the longitudinal axis of the hole, inserting the anchor in the hole such that the sidewalls of the hole elastically deform the barbs, and thereafter withdrawing the tool from the deployed anchor assembly.

37 Claims, 3 Drawing Sheets

SUTURE ANCHOR AND INSTALLATION TOOL

This is a continuation of copending application(s) Ser. No. 07/766,025 filed on 09/26/91 now abandoned.

FIELD OF THE INVENTION

This invention relates generally to fastening devices. More particularly, the invention relates to anchoring devices of the sort adapted to fixedly locate one end of an object in a workpiece, and installation tools for deploying the same. Still more particularly, the invention relates to suture anchors of the sort adapted to anchor one end of a piece of conventional suture in bone, and installation tools for deploying the same.

BACKGROUND OF THE INVENTION

In U.S. Pat. No. 4,898,156, entitled "Suture Anchor"; U.S. Pat. No. 4,899,743, entitled "Suture Anchor Installation Tool"; and U.S. Pat. No. 4,968,315, entitled "Suture Anchor and Suture Anchor Installation Tool" (each of which is presently owned by Mitek Surgical Products, Inc., of Norwood, Mass., the assignee of this application), there are disclosed a variety of anchors of the sort adapted to anchor one end of a piece of conventional suture in bone. These patents further disclose several anchor installation tools for deploying the suture anchors therein disclosed. Complete details of the construction and use of these various anchors and anchor installation tools are provided in the specifications and drawings of the above-identified U.S. Patents. Those specifications and drawings are hereby incorporated by reference into the present application.

It, therefore, will be understood that anchoring devices of the type including a coupling member and at least one curved barb extending upwardly and outwardly from an end of the coupling member are known in the art. It also will be understood that tools for deploying such anchoring devices in holes in surfaces of workpieces similarly are known in the art. As the requirements of users of such devices, particularly in the medical field, have become more demanding, however, known anchoring devices and installation tools therefor have encountered problems. Particular among these problems are (1) the possibility of known anchors to fail (i.e., to become dislodged), (2) the diameter of the anchor-receiving hole in the workpiece required for deployment of the anchor, (3) the need for precise location of the barb(s) both during anchor insertion and at final deployment to avoid damage to delicate structures (such as a joint) adjacent to the hole, and (4) in multibarb configurations, the need for deployment means which assure the central location of the coupling member of the anchor within the anchor-receiving hole during the insertion operation, at least until the engagement of the respective outer barb ends with the sidewall of the hole at substantially equal depths is achieved. The reasons for these problems will become apparent in the following general synopsis of these known anchoring systems.

As noted above, anchors are known which include a coupling member and at least one barb extending upwardly and outwardly from an end of the coupling member. The coupling member generally comprises a piece of 6A14V titanium alloy having a first end surface, a second end surface and a longitudinal axis. The first end surface lies in a plane substantially normal to the longitudinal axis, while the plane of the second surface may be either normal to, or located at an acute angle to, the longitudinal axis. In either alternative, suture attachment means are associated with the second surface. Such attachment means may take several forms. For example, a blind hole may extend centrally into the second surface. The blind hole is adapted to receive a knot formed in one end of the suture. The blind hole also may be connected to the periphery of the coupling member by a slot in order to allow the free end of the suture to extend more easily toward the first end of the coupling member and then out of the hole wherein the anchor is located.

Alternatively, a bore may extend substantially normally into a second surface lying in a plane located at an acute angle to the longitudinal axis. In that case, the bore extends through the coupling member so as to exit at a portion of its sidewall between the first and second ends on the opposite side of the coupling member from that over which the barb extends. A suture may extend through this bore and then substantially directly upwardly toward the open end of the anchor-receiving hole. A knot at the end of the suture threaded through the bore, engaging the second surface, assures the secure connection to the anchor of an object attached to the other end of the suture. In another alternative, the coupling member may define a longitudinal bore therethrough which allows an end of a suture to extend longitudinally through the coupling member for securement to the second surface, for example by the formation of a knot adapted to bear against the second surface adjacent the opening of the bore therein.

As will become apparent below, this tendency in the art of associating the attachment of the suture with the second end of the coupling member can be a source of difficulty to known anchors of the type described. Further, the secure attachment of the object to the workpiece surface with a single suture strand can be difficult. If proper tension is not maintained both during the attachment process and thereafter, the object may move relative to the workpiece, thereby possibly causing damage to adjacent structures.

At least one curved barb extends upwardly and outwardly from the first end of the coupling member in these known anchors. The barb is commonly formed of a length of nickel titanium alloy wire which in its unrestrained state defines an arc having a radius greater than the radius of the coupling member. The barb may be formed integrally with the coupling member, but more commonly one end of the wire extends into a hole in the first surface. In the latter case, the exterior of the coupling member commonly is crimped adjacent to the hole to assure the fixed location of the wire end therein. Also in the latter alternative, at least about 90 degrees of the arc of the barb remains unrestrained by the hole in the first surface of the coupling member. The nickel titanium alloy is chosen such that the barb is capable of being elastically deformed to a substantially straight configuration when desired (i.e., so that the barb's second end can be shifted from its location radially outboard of the sidewall of the coupling member when the free end of the barb is unrestrained to a location in general alignment with the end of the barb engaging the hole in the first end of the coupling member). By way of example, the barb may be made out of binary nitinol such as that sold by Furukawa of Japan and Raychem Corporation of Menlo Park, Calif., or it might be made out of ternary nitinol such as that sold by Raychem Corporation and described in U.S. Pat. No. 4,505,767 (Quinn).

Anchors of the type just described are deployed in holes in the surfaces of workpieces and connected to objects lying on the surface of the workpiece adjacent the hole. Various tools have been developed to accomplish this deployment. In one form, the tool included three mutually telescoping elements; namely, an outer insertion cannula, a suture anchor loader adapted to telescope within the insertion cannula, and a plunger adapted to telescope within the suture anchor loader. The coupling member is inserted into the proximal end of the outer insertion cannula with the unrestrained barb extending out of the proximal end of the outer insertion cannula. Next, the barb is inserted into the distal end of the suture anchor loader, and the loader is telescoped down into its outer insertion cannula. This causes the barb to be deformed into a substantially straight configuration within the central bore of the loader. Next, the plunger is telescoped into the loader until its distal end contacts the proximal end of the deformed barb. Then the distal end of the insertion tool is located within the hole in the workpiece adjacent the desired anchor location. Finally, the plunger is driven towards the distal end of the insertion cannula, so as to drive the anchor out of the insertion tool and into the workpiece at the desired location. See U.S. Pat. No. 4,898,156 identified above.

Subsequently, it was realized that anchor-receiving hole diameters could be reduced by allowing the sidewall of the hole in the workpiece to deform the barb(s) as the anchor is inserted. The outer insertion cannula and plunger, therefore, were deleted, and a longitudinal slot was provided adjacent to the distal end of the anchor loader adapted to permit the barb to extend radially outwardly from the loader when the anchor is inserted into its loading end. The engagement of the barb with the sidewall of the hole allows the anchor loader to be pulled out of the hole in the workpiece, leaving the anchor in place. See U.S. Pat. No. 4,899,743 identified above.

Still later, in response to a desire for improved engagement between the insertion tool and the suture anchor, as well as in response to other desires such as improved suture attachment and workpiece hole diameters, the diameter of the portion of the coupling member adjacent to its first surface was reduced relative to the diameter of the remainder of the coupling member. This construction allows the reduced-diameter portion of the suture anchor to be received within the insertion tool, yet permits the diameter of the anchor loader to be reduced to that of the larger portion of the coupling member. See U.S. Pat. No. 4,968,315.

Certain problems can be encountered with bone anchors of the sort disclosed in U.S. Pat. Nos. 4,898,156; 4,899,743; and 4,968,315, when only one barb is provided and the suture is attached to the second end of the coupling member (i.e., at the end of the coupling member opposite to that which the single barb is attached to), and the second end of the coupling member is disposed at an acute angle relative to the longitudinal axis of the coupling member. For one thing, with such bone anchors, the suture generally extends parallel to, and external of, at least a portion of the bone anchor during insertion into the workpiece. In some circumstances, friction between the workpiece and the coupling member and/or the insertion tool can damage or even sever the suture during insertion. For another thing, in certain types of soft workpieces, e.g. diseased bone, applying a load to the suture attached to the distal end of the suture anchor (i.e., to the angled second end of the coupling member) can cause the suture anchor to pivot in the workpiece, about the proximal end of its barb, thereby possibly becoming dislodged. Furthermore, particularly with suture anchors of the sort disclosed in U.S. Pat. No. 4,968,153, which attach the barb to a reduced diameter first end portion, the provision of multiple barbs can cause the size of the suture anchors to significantly increase, which can be undesirable.

OBJECTS OF THE INVENTION

Accordingly, it is an object of the present invention to provide a novel anchor configuration having improved anchoring characteristics.

It is also an object of the present invention to provide a novel anchoring system which minimizes the workpiece hole size requirements for anchor deployment.

Further, it is an object of the present invention to provide an anchor and anchor installation tool which improve upon the anchor and anchor installation tools shown in U.S. Pat. Nos. 4,898,156; 4,899,743; and 4,968,315.

Still further, it is an object of the present invention to provide a novel method for deploying an anchor in a workpiece.

Yet another object of the present invention is to provide a suture and anchor assembly which will permit the suture to make a slipping engagement with a deployed anchor, so as to facilitate manipulation of suture throws positioned about the free end of the suture down the length of suture, so as to approach the workpiece in which the anchor is located.

SUMMARY OF THE INVENTION

These and other objects and advantages of the present invention are achieved through the use of a novel anchoring system including an anchor assembly and an anchor installation tool.

The novel anchor assembly includes a coupling member, at least two barbs and attachment means. The coupling member comprises a body having a longitudinal axis. The body includes a first portion having a first end, a second portion having a cross-section (transverse to the longitudinal axis) smaller than the cross-section (transverse to the longitudinal axis) of the first portion, and a middle portion connecting the first and second portions. The middle portion includes at least two equally-circumferentially-spaced channels separated by walls, the channels and walls both extending from the first end of the first portion to one end of the second portion. The barbs extend in equally spaced circumferential relation to each other, and in equally spaced radial relation to said longitudinal axis, from the first end of the first portion adjacent the closed ends of the respective channels to respective outer ends substantially radially displaced from the body. Each barb is curved in its normal unstressed state, but is capable of being elastically deformed to a substantially straight configuration substantially parallel to the longitudinal axis of the body. The outer edges of the walls of the middle portion adjacent the second portion respectively define equally-circumferentially-spaced indented portions on the outer surface of the body. The base of each of these indented portions is substantially the same distance from the longitudinal axis of the body as the adjacent outer surface of the second portion of the body. The attachment means are directly associated with the second portion of the body. In a preferred embodiment, the attachment means comprise a diametrical round or elongated hole extending through the second portion and the middle portion. In addition, in a preferred embodiment, each of the barbs is sized so that when it is deformed to a substantially straight configuration, the proximal end of the barb will terminate short of the proximal side of the diametrical hole forming the attachment means, so as to prohibit any engagement between the proximal end of the barb and a suture passing through the hole.

The foregoing anchoring assembly is used with a novel installation tool which generally comprises an elongated shaft having a distal end, a proximal end and a transverse cross-section substantially the same as that of the first end portion of the body of the coupling member. In a preferred embodiment, this cross-section is maintained proximally from the distal end of the shaft for at least a predetermined distance sufficient to allow deployment of the anchoring assembly within a minimum diameter hole formed in a workpiece. The remainder of the shaft may have a larger cross-section to thereby render it stronger and provide a ledge surrounding the exterior of the shaft useful in assuring the deployment of the anchor assembly at a predetermined depth within a hole in the workpiece. Also, a handle is attached to the proximal end of the shaft in the preferred embodiments. Further, a bore sized to receive the second end portion of the body extends centrally into the distal end of the shaft to a depth slightly greater than the longitudinal length of the second portion of the body. A pair of slots extend through the walls of the bore in equally spaced circumferential relation to each other. Finally, projections having substantially the same cross-section as the indentations on the outer surfaces of the walls of the middle portion of the body of the coupling member extend in equally spaced circumferential relation to each other distally from the walls of the bore, substantially midway between the slots and adjacent the exterior of the shaft.

The method of deploying the anchor assembly within a workpiece contemplated by the present invention includes (1) the provision of the above anchoring system components; (2) the formation of a hole in the surface of a workpiece; (3) the attachment of an object (or connecting member) to the attachment means; (4) the telescopic insertion of the second end portion of the body of the coupling member into the bore at the distal end of the shaft of the insertion tool such that the projections from the distal end of the insertion tool engage the indentations in the outer surface of the middle portion of the body of the coupling member; (5) the insertion of the anchor assembly into the hole by the application of a pushing force to the anchoring assembly by the installation tool to drive it a desired distance into the hole in the workpiece such that the sidewalls of the hole deform the barbs into their substantially straight configuration within the channels of the middle portion of the body; and (6) the withdrawal of the installation tool from its engagement with the anchor assembly and from the hole.

BRIEF DESCRIPTION OF THE DRAWINGS

These and other features, objects and advantages of the present invention will be described in, or become obvious to those skilled in the art in view of, the following detailed description of the invention which is to be considered in light of the accompanying drawings in which like reference numerals are used to designate like elements throughout, and further in which.

DETAILED DESCRIPTION OF THE PREFERRED EMBODIMENT

It is to be understood at the outset that the surgical context of use of the present invention which appears in the following description has been selected for convenience of illustration only. Certain features and advantages of the invention are particularly beneficial in this context, and certain modifications of the invention in its broader aspects have been developed with specific reference to its surgical utility. No limitation of the invention in its broader aspects is intended by the choice of this context for the following description, and none should be implied therefrom. Similarly, no limitation of the present invention is intended from the choice of descriptive terms for any of the elements discussed below, and none should be implied therefrom.

Figures 1, 2, 3:
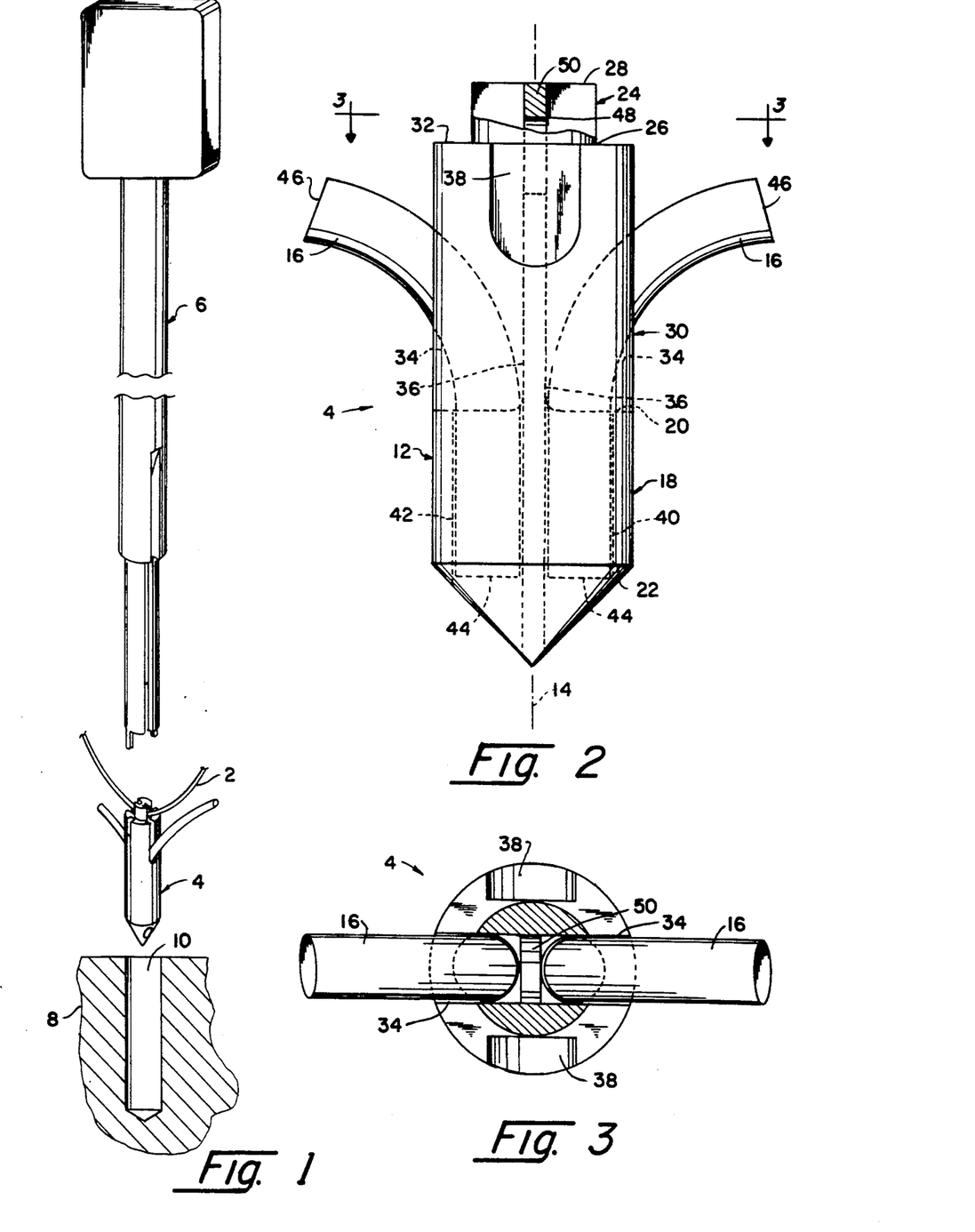
FIG. 1 is a perspective view showing a suture and suture anchor assembly, an installation tool adapted for use with the suture and suture anchor assembly, and a target bone which is to receive the suture anchor assembly, all in exploded relation to one another.
FIG. 2 is a side elevational view in partial section of a suture anchor assembly in accordance with the present invention.
FIG. 3 is a cross-sectional view of a suture anchor assembly taken along the line 3—3 of FIG. 2.

Referring now to the drawings, and particularly to FIG. 1, there is shown an exploded perspective view of a suture 2 attached to a suture anchor assembly 4, an installation tool 6 particularly adapted for use with the anchor assembly 4, and a target bone 8 having a hole 10 formed therein for receipt of the anchor assembly 4. The anchor assembly 4, the associated installation tool 6, and a method for deploying the anchor assembly in a hole formed in a workpiece now will be separately described.

The anchor assembly 4 (best seen in FIGS. 2 and 3) includes a body 12 having a longitudinal axis 14 and at least two identical barbs 16. Specifically, the body 12 has (a) a first portion 18 having a first end 20 and an outer end 22, (b) a second portion 24 having an inner end 26, an outer end 28, and a cross-section (transverse to the longitudinal axis 14) smaller than the cross-section (transverse to the longitudinal axis) of the first portion 18, and (c) a middle portion 30 connecting the first end 20 of the first portion 18 to the inner end 26 of the second portion 24. Second portion 24 is centered about the longitudinal axis 14 such that a radially-outwardly-projecting ledge 32 is formed adjacent inner end 26 of second portion 24 by middle portion 30. At least two equally-circumferentially-spaced radial channels 34 in the exterior of body 12 extend from the first end 20 of the first portion 18 to the outer end 28 of second portion 24. In the embodiment shown in FIGS. 1-3, 5 and 6, there are two such channels each having a width of approximately 0.033 inches and a depth (measured in the middle portion 30) of approximately 0.041 inches. In fact, there are always exactly as many channels 34 as there are barbs 16 on the anchor assembly. Thus, in the embodiment shown in FIGS. 1-3, 5 and 6, there are two channels 34. It will be understood that the interior bases 36 of the channels 34 so defined are carried substantially parallel to the longitudinal axis 14 to the outer end 28 of the second portion 24.

The outer surface of middle portion 30 is indented adjacent ledge 32 to form a pair of grooves 38. Grooves 38 are diametrically opposed to one another, and are positioned equidistant between channels 34. In the embodiment shown in FIGS. 1-3, 5 and 6, grooves 38 have a depth substantially equal to the radial width of ledge 32, and extend longitudinally along the outer surface of middle portion 30 slightly less than one-half of the total longitudinal length of the middle portion 30. In a specific example, the depth of the grooves 38 is approximately 0.016 inches, their length is approximately 0.070 inches, and their width is approximately 0.044 inches.

Longitudinal bores extend parallel to the longitudinal axis 14 into the first end 20 of the first portion 18 adjacent the bases 36 of each of the slots 34. In the embodiment shown in FIGS. 1-3, 5 and 6, there are two such bores shown at 40 and 42 respectively. In fact, there are always exactly as many of these bores as there are barbs 16 on the anchor assembly. Thus, in the embodiment shown in FIGS. 1-3, 5 and 6, there are two bores 40 and 42. Also in the embodiment shown in FIGS. 1-3, 5 and 6, representative dimensions of the body may be as follows: the diameter of the first and middle portions of the body is approximately 0.093 inches, the diameter of the second portion is approximately 0.060 inches, the longitudinal length of the first portion is approximately 0.072 inches, the longitudinal length of the middle portion is approximately 0.148 inches, and the longitudinal length of the second portion is approximately 0.050 inches. The diameters of the bores 40 and 42 are both approximately 0.030 inches, and they extend from the first end 20 of the first portion 18 all the way through the first portion 18 to its outer end 22. Of course, bores 40 and 42 may extend into first end 20 only part of the way longitudinally through first portion 18 without departure from the present invention.

The barbs 16 each are formed by a length of nickel titanium alloy having a first end 44 and a second end 46. Such materials are readily available commercially from Raychem Corporation and GAC International, Inc., among others. The first ends 44 of the respective barbs are attached to the first end 20 of the first portion 18 so that they respectively extend axially and radially outwardly therefrom. In a preferred embodiment, the barbs 16 have a diameter of approximately 0.026 inches, and in their unrestrained state define an arc of approximately 90 degrees of loop approximately 0.143 inches in diameter (when measured to the inside edge of the loop). Each barb 16 also is capable of being elastically deformed to a substantially straight configuration when desired such that its first end 44 is substantially aligned with its second end 46 in a line substantially parallel to the longitudinal axis 14. The length of the barbs 16 in the embodiment shown in FIGS. 1-3, 5 and 6 is less than or equal to the longitudinal length of the body 12 measured from the outer end 28 of the second portion 24 to the outer end 22 of the first portion 18. The barbs may be made integrally with the body 12, however, in the preferred embodiment the first ends 44 of the barbs 16 are inserted into the bores 40 and 42 respectively such that they extend all the way therethrough to the outer end 22 of the first portion 18. The tendency of the respective barbs to return to their curved configuration acts to hold the portions of the barbs inserted in the straight bores within the bores. The permanence of this engagement may be further assured by crimping the first portion 18 of the body 12 adjacent the bores, or otherwise mechanically locking a portion of the respective barbs within the respective bores.

Attachment means 48 are associated with the second portion 24. In the embodiment shown in FIGS. 1-3, 5 and 6, attachment means 48 is a bore extending transverse to the longitudinal axis 14 through the wall 50 which is located between the respective bases 36 of the slots 34 adjacent the inner end 26 of the second portion 24. Permissibly, this bore may extend partially into the adjacent middle portion 30 in order to allow the passage of a suture or some other connecting object therethrough while maintaining the structural integrity of the outer end 28 of second portion 24 and the required strength of wall 50. It will be understood that the purpose of the attachment means 48 is to allow the attachment of an object or a connecting means to the second portion 24 such that forces tending to withdraw the body from an anchoring position are applied substantially along the axis 14. The dislodging torque induced by applied withdrawing forces in prior suture anchors are thereby avoided, and a greater portion of the maximum anchoring power of the anchor assembly is utilized.

Figure 4A:
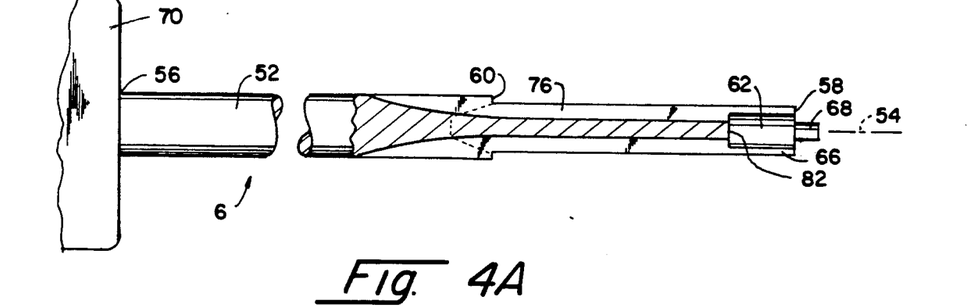
FIG. 4A is a side elevational view of an installation tool suitable for use with the suture anchor assembly of FIG. 2 in accordance with the present invention.
Figure 4B:
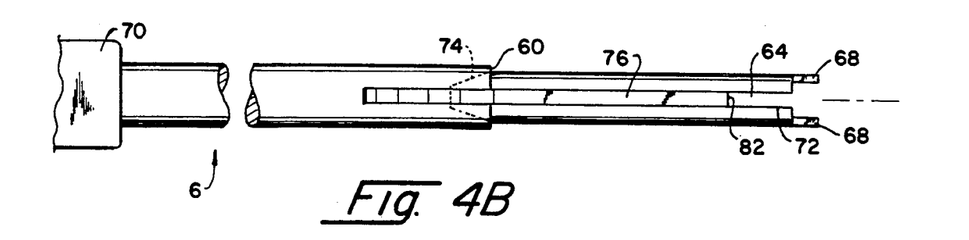
FIG. 4B is a top elevational view of the tool of FIG. 4A.
Figures 4C, 5, 6:
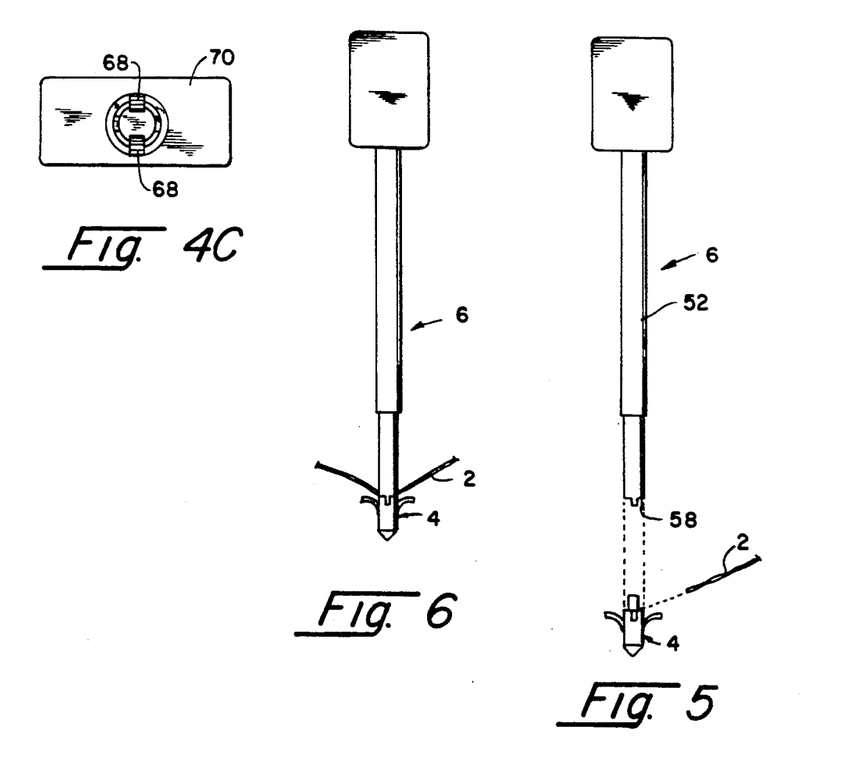
FIG. 4C is a right end elevational view of the installation tool of FIG. 4A.
FIG. 5 is an exploded perspective view of a suture, a suture anchor, and an insertion tool in accordance with the invention.
FIG. 6 is a perspective view of the suture, suture anchor and installation tool of FIG. 5, with the various elements assembled together.

The anchor assembly just described is particularly adapted to be utilized in conjunction with an installation tool 6. Tool 6, best seen in FIGS. 4A, 4B and 4C, is preferably (but not necessarily) made of 17-4PH stainless steel, annealed. Generally, it includes an elongate shaft 52 having a longitudinal axis 54, a proximal end 56 and a distal end 58. The shaft 52 has a cross-section (transverse to the longitudinal axis 54) substantially the same as the cross-section (transverse to the longitudinal axis 14) of the first portion 18 of the body 12. If desired, this cross-section need only be maintained for a predetermined distance proximally of the distal end 58. It is contemplated that the latter alternative will allow the proximal portion of the shaft to be provided with greater rigidity and strength, and that the provision of a predetermined location of the change in cross-section size may be utilized to form a circumferential ledge or stop 60 about the shaft useful in the precise location of an anchor assembly in a hole for a workpiece.

A bore 62 having a cross-section (transverse to the longitudinal axis 54) substantially the same as the cross-section (transverse to the longitudinal axis 14 of second portion 24) of anchor body 12 extends centrally into distal end 58 of shaft 52 to a depth at least slightly greater than the longitudinal length of second portion 24 of anchor body 12. In the embodiment shown in FIGS. 1-3, 5 and 6, bore 62 is cylindrical in cross-section and has a depth of approximately 0.056 inches. Two equally-circumferentially-spaced slots 64 extend through the sidewall 66 of the bore 62. Slots 64 have a longitudinal length substantially the same as the depth of bore 62 and a width substantially the same as the width of channels 34 in the middle portion 30 of the body 12. Furthermore, slots 64 have a width sufficient to accommodate a suture or other object extending through attachment means 48. Substantially midway between slots 64, two projections 68 extend outwardly from the periphery of the distal end 58 of the shaft 52. The cross-section of each projection 68 (measured transverse to the longitudinal axis 54) is substantially the same as the cross-section (measured transverse to the longitudinal axis 14) of the indented portions 38. The longitudinal length of each projection 68 is less than the longitudinal length of the indented portions 38. Preferably the leading tips of projections 68 are rounded slightly to facilitate entry into indented portions 38, as will hereinafter be discussed in further detail. Also, a handle 70 having a rectangular cross-section (transverse to the longitudinal axis 54) is affixed to the proximal end 56 of the shaft 52 such that the planes containing two opposite sides of the handle are preferably parallel to the plane containing the side edges 72 of at least one of the slots 64.

The installation tool 6 is particularly adapted for the deployment of an anchor assembly such as that shown at 4 within a hole in a workpiece (see FIG. 1). Obviously, different anchor assembly cross-sections will require different tools, or at least modifications of a basic tool, particularly related to the anchor assembly to be deployed. In this regard, it is contemplated that the distal portion of the shaft 52 could be made separately from the proximal portion thereof (as illustratively shown in dotted lines 74 in FIG. 4B). The distal portion might then be provided with a tapered proximal end including a locking mechanism such as a key (not shown) adapted to engage a tapered bore and keyway (not shown) in the distal end of the proximal portion of the shaft, to thereby lock the elements of the installation tool together.

The method of use of the anchoring system of the present invention now will be described in the context of the attachment of a suture to a bone. The suture 2 is first attached to the attachment means by threading it through the hole 48, as shown in FIG. 5. In the preferred case, both ends of the suture remain free, however, if desired, a knot may be formed in one end for engagement with one side of the wall 50 while the other end extends freely from the other side of wall 50. Thereafter, the anchor assembly 4 is attached to the distal end 58 of the shaft 52 as shown in FIGS. 5 and 6. The latter step is accomplished by (a) aligning the longitudinal axis 14 of the anchor assembly body 12 with the longitudinal axis 54 of the shaft 52, (b) aligning the projections 68 extending from the distal end 58 of the shaft 52 with the indentations 38 on the outer surface of the middle portion 30 of the anchor assembly body 12, and (c) sliding the second portion 24 of the anchor assembly body 12 into the bore 62 in the distal end 58 of the shaft 52 while at the same time sliding the projections 68 from the distal end 58 of the shaft 52 into the indentations 38 on the outer surface of the middle portion 30 of the anchor assembly body 12.

The resulting two stage joinder of the anchor assembly to the distal end of the shaft 52 is secure, resistant to accidental disengagement, and automatically aligns the barbs in a predetermined spatial relationship to the handle. This is important, because without the presence of the projections 68 engaging the middle portion 30, the anchor assembly body 12 might be vulnerable to accidental dislodgement from the shaft 52. It is not uncommon for the anchor assembly/installation tool combination to be assembled (and sterilized where appropriate) prior to the start of a surgical procedure during which an anchor assembly will be deployed. It also is not uncommon for the anchor assembly to be subjected to forces tending to dislodge the anchor from the tool during preparation for the surgical procedure and/or during the initial stages of the deployment procedure (i.e., prior to the anchor assembly reaching the hole in the bone in which it is to be deployed). Such dislodgement of the anchor assembly is inconvenient, and may be costly in the event that the anchor assembly is either lost or must be resterilized prior to use. The present invention avoids these potential problems. The slotted sidewalls of the bore 62 in the distal end of the shaft 52 act like resilient fingers grasping the second portion 24 of the anchor assembly body, and the projections 68 from the distal end 58 of the shaft 52 act like resilient fingers grasping the middle portion 30 of the anchor assembly body. Since the fit between these elements is relatively tight, there is little chance of accidental axial dislodgement. Further, since radially directed dislodging forces tend to act around the distal end of the shaft, the re-enforcement of the joinder in two different planes (i.e., the plane passing through the diametrically opposed projections 68 and the plane passing through the two diametrically opposed slotted sidewalls of the bore 62) reduces the chance of accidental dislodgement of the anchor assembly. Hence, the surgeon is free to treat the loaded shaft as a unit, thereby facilitating the operative procedure.

Figure 7:
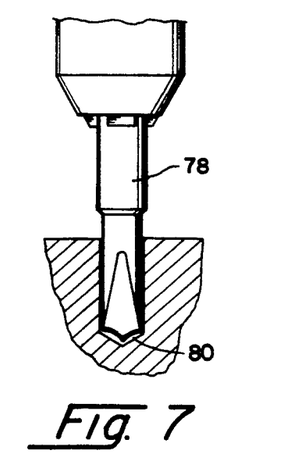
FIG. 7 is a side elevational view of a novel drill in accordance with the present invention forming a hole in a workpiece which is to receive an anchor assembly.

The anchor assembly then is deployed in a predrilled hole in the bone by inserting the outer end 22 of the first portion 18 of the anchor assembly (which may be generally pointed, as illustrated in the drawings, if desired) into the hole, and thereafter exerting an axial pushing force on the proximal handle portion 70 until the outer end 22 of the first portion 18 of the anchor assembly bottoms out against the bottom of the hole or the anchor assembly otherwise reaches a desired depth within the hole, e.g. by engagement of the stop 60 with the upper surface of the bone 8. During insertion, the suture 2 threaded through hole 48 can be received in slots 64 and their continuations 76 (see FIGS. 4A and 4B), so as to minimize any contact between the suture and bone 8. It has been found that forming the hole with a drill 78, such as that shown in FIG. 7, having distal cutting surfaces 80 which taper inwardly from the outer diameter of the drill toward its longitudinal axis, is beneficial. In that instance, the hole defines a generally conical volume at its bottom. The provision of a generally matching configuration to the outer end 22 of the first portion 18 of the anchor assembly body 12, permits undesirable pivoting of the anchor assembly within the hole to be avoided.

Also, as the distal end of the shaft 52 forces the anchor assembly 4 into the hole, the barbs 16 engage the sidewalls of the hole and are forced to retract into the grooves 34. The secure joinder of the anchor assembly to the distal end of the shaft is important at this stage as well. It prevents accidental dislodgement of the anchor in response to attempts to deploy the anchor which are not in good alignment with the axis of the hole. Further, it assures that the body 12 of the suture anchor does not pivot in the hole during the deployment operation. If such were to occur, one of the barbs might engage the sidewall of the hole at a different depth than the other barb(s). In such an event, the higher barb would return further toward is unrestrained state and provide a smaller engagement force with the sidewall of the hole than the other barb(s). The holding power of the anchor would be reduced accordingly, particularly because withdrawal forces applied to the attachment means would no longer be equally distributed among the barbs.

Another advantage of this invention is that the hole size required in the workpiece may be minimized. As will be recognized from the drawings, the dimensions of the first portion 18 of the anchor assembly body 12 are such that the two required barbs 16 are supportable by the first surface 20 of the first portion 18, with an attachment capability extending proximally and axially outwardly between them. Further, by providing the shaft of the installation tool with longitudinal grooves 64 and 76, wherein the grooves 76 extend proximally from the base 82 of the bore 62 in alignment with the slots 64 in the sidewall 66 of the bore, it is possible to contain the suture within the periphery of the shaft until it exits the bone hole. Accordingly, the hole diameter need only define a circular cross-section which will contain the cross-section of the first portion 18 of the body 12 of the anchor, without fear of the suture being damaged through a shearing engagement with bone 8 and suture anchor 4 and/or installation tool 6. Still further, the barbs 16 are not held exactly parallel to the longitudinal axis 14 of the anchor assembly body 12 by the sidewalls of the grooves 34. Instead, their outer ends 46 bear against the sidewalls of the hole 10 which are radially displaced from the point from which the barbs 16 arise from the first surface 20 of the first portion 18. This, combined with the inability for the anchor assembly to pivot in the hole and the change in location of the application of withdrawing forces provided by the invention, all co-act to provide an improved anchor.

Further variations, modifications, alterations, changes and the like will occur to those skilled in the art in light of the foregoing description of the invention.

Figure 8:
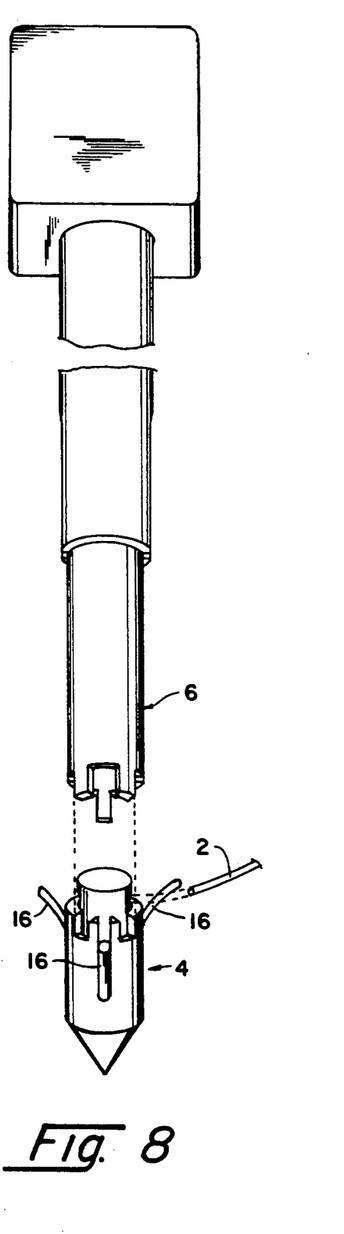
FIG. 8 is an exploded perspective view of another anchor assembly and installation tool in accordance with the present invention.

For example, the anchor assembly may be provided with more than two barbs, and the insertion tool modified to accommodate the modified anchor assembly, as illustratively shown in FIG. 8. A detailed and complete discussion of this alternative would be largely redundant of the foregoing discussion and, therefore, will not be undertaken here.

Figure 9:
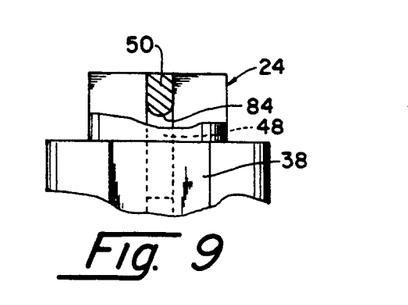
FIG. 9 is a partial, enlarged side elevational view in partial section showing the proximal end of another suture anchor.

Furthermore, as shown in FIG. 9, the portion of the wall 50 forming the proximal end of hole 48 may be rounded as shown at 84, to facilitate a smooth loading of the suture 2 against the surface 84. This will minimize any possibility of abrading or creasing or otherwise damaging the suture 2 when it is subjected to a load. Furthermore, the provision of such a smooth surface 84 will facilitate the ability of the suture to make a slipping engagement with a deployed suture anchor. This can aid the user in the manipulation of suture throws positioned about the free end of the suture down the length of suture, so as to approach the workpiece in which the anchor is loaded. It should be further appreciated that the ability of the suture to make a slipping engagement with a deployed suture anchor is also enhanced since the reduced diameter second portion 24 positions the suture inboard of, and interior to, the surrounding bone 8, thereby minimizing engagement of the suture with bone 8 during manipulation of suture throws.

Figure 10:
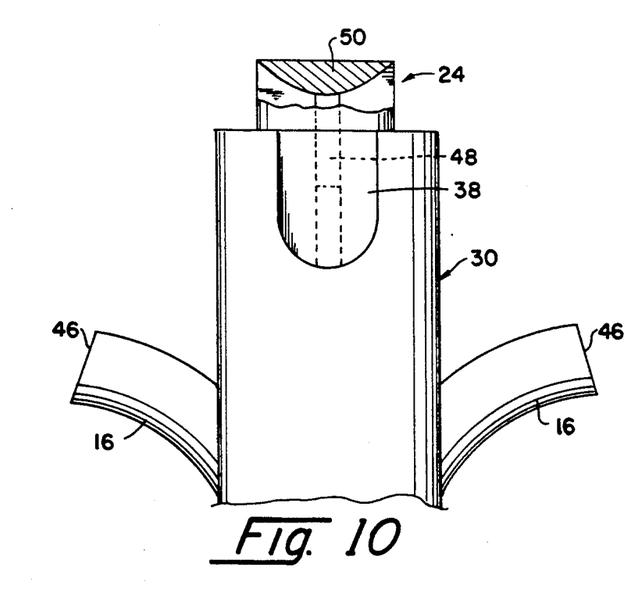
FIG. 10 is a partial, enlarged side elevational view in partial section showing the proximal end of yet another suture anchor.

Furthermore, the length of middle portion 30 of suture anchor 4 could be increased, so that the proximal end of hole 48 terminates well above the ends 46 of the barbs 16 when the barbs are deformed to their substantially straight configuration during anchor insertion. See FIG. 10. Such a construction will minimize any possibility that barbs 16 might engage, and thereby damage, suture 2 during the insertion process. Furthermore, as also seen in FIG. 10, it is anticipated that one might terminate channels 34 short of the outer end 28 of second portion 24, and broaden the contour of wall 50 so as to extend across the full width of outer end 28 and thereby provide an enlarged suture-bearing surface.

Additionally, it is anticipated that one might extend hole 48 down a significant distance along axis 14 so that the distal end of hole 48 approaches first end 20 of first portion 18. This will have the effect of permitting channels 34 to communicate with one another along a greater portion of their length than as shown in FIG. 2.

As alluded to previously, it is not the intention of the foregoing description to be restrictive of the invention. The description is rather intended to be illustrative only. The invention, therefore, should be understood as being restricted only by the terms of the appended claims.

What is claimed is:

1. Apparatus for attaching an object to a workpiece comprising:

an anchor assembly comprising a body and at least two barbs;

said body having a longitudinal axis, a first portion having a first end and a second end and a first maximum cross-section transverse to said longitudinal axis, a second portion centered on said longitudinal axis having a first end and a second end and a second cross-section transverse to said longitudinal axis smaller than said maximum cross-section of said first portion, and a middle portion having a first end and a second end, said second end of said first portion being joined to said first end of said middle portion, and said first end of said second portion being joined to said second end of said middle portion, said middle portion defining at least two equally-circumferentially-spaced channels extending inwardly from an axial projection of said maximum transverse cross-section of said first portion to a base adjacent said longitudinal axis, and said channels extending longitudinally between said second end of said first portion and said second end of said middle portion, said channels being separated by longitudinal walls extending radially of said longitudinal axis to an outer surface located on said axial projection of the periphery of said maximum transverse cross-section, and said middle portion defining at least two axial grooves extending from said second end of said middle portion towards said first end of said middle portion;

one of said barbs extending axially and radially outwardly from said second end of said first portion adjacent the base of each said channel to an outer end located radially outwardly of said axial projection of said first maximum transverse cross-section of said first portion, each said barb being curved in its normal unrestrained state but capable of being elastically deformed into a substantially straight configuration with its outer end located radially within said axial projection of said first maximum transverse cross-section of said first portion; and attachment means associated with said second portion for connecting an object to said anchor assembly.

2. A system for attaching an object to a workpiece comprising:
   a) means for forming a hole in said workpiece; b) an anchor assembly comprising a body and at least two barbs;
      said body having a longitudinal axis, a first portion having a first end and a second end and a first maximum cross-section transverse to said longitudinal axis, a second portion centered on said longitudinal axis having a first end and a second end and a second cross-section transverse to said longitudinal axis smaller than said maximum transverse cross-section of said first portion, and a middle portion having a first end and a second end, said second end of said first portion being joined to said first end of said middle portion, and said first end of said second portion being joined to said second end of said middle portion,
      said middle portion defining at least two equally-circumferentially-spaced channels extending inwardly from an axial projection of the periphery of said first maximum transverse cross-section of said first portion to a base adjacent said longitudinal axis, and said channels extending longitudinally between said second end of said first portion and said second end of said middle portion, said channels being separated by longitudinal walls extending radially of said longitudinal axis to an outer surface located on an axial projection of the periphery of said first maximum transverse cross-section,
      said middle portion defining at least two axial grooves extending from said second end of said middle portion towards said first end of said middle portion;
      one of said barbs extending axially and radially outwardly from said second end of said first portion adjacent the base of each said channel to an outer end located radially outwardly of said axial projection of said maximum transverse cross-section of said first portion, each said barb being curved in its normal unrestrained state but capable of being elastically deformed into a substantially straight configuration with its outer end located radially within said axial projection of said first maximum transverse cross-section of said first portion; and
      attachment means associated with said second portion for connecting an object to said anchor assembly; and
   c) an insertion tool for deploying said anchor assembly in said hole in said workpiece, said tool comprising an elongate shaft having an exterior surface, a second longitudinal axis, a proximal end, a distal end, a cross-section transverse to said second longitudinal axis substantially the same as said first maximum transverse cross-section of said first portion of said anchor assembly, a bore having a cross-section transverse to said second longitudinal axis substantially the same as said second cross-section of said second portion of said anchor assembly and extending centrally into said distal end of said shaft, said bore being adapted to slidably receive said second portion of said anchor assembly and defining at least two equally-circumferentially-spaced slots extending between said bore and said exterior surface of said shaft, and at least two projections, each projection having substantially the same cross-section transverse to said second longitudinal axis as said cross-sections transverse to said first longitudinal axis of said grooves formed in said middle portion of said anchor assembly so as to be slidably receivable in one of said grooves.

3. The apparatus of claim 2 wherein said barbs are made of nickel titanium alloy.

4. The apparatus of claim 2 wherein said first portion of said body defines at least two bores extending longitudinally from said second end of said first portion towards said first end of said first portion, one bore adjacent the base of each said channel, and wherein each of said barbs is a piece of wire having a first end and a second end, said first end of each said wire fixedly engaging one of said bores in said second end of said first portion.

5. The apparatus of claim 4 wherein the longitudinal length of said body measured parallel to its longitudinal axis is substantially the same as the length of said pieces of wire when said wire is deformed into its substantially straight configuration.

6. The apparatus of claim 2 wherein there are two barbs and wherein said attachment means comprises a bore having a third longitudinal axis extending through said second portion, said third longitudinal axis being located in the plane containing said first longitudinal axis and a diameter of both of said barbs measured along said second end of said first portion.

7. The apparatus of claim 6 wherein said attachment means further includes a cord-like connecting element threaded through said bore of said attachment means so as to securely engage said attachment means and provide at least one free end for attachment to said object.

8. The apparatus of claim 2 wherein said insertion tool is made of stainless steel.

9. The apparatus of claim 2 wherein there are three barbs and three channels.

10. The apparatus of claim 2 wherein said anchor assembly is made of titanium alloys.

11. The apparatus of claim 2 wherein all of said cross-sections are substantially circular.

12. The apparatus of claim 2 wherein a handle is attached to said proximal end of said shaft.

13. The apparatus of claim 12 wherein said handle includes means for determining the spatial orientation of said barbs in said workpiece.

14. The apparatus of claim 2 wherein said means for forming a hole in said workpiece comprises a drill.

15. The apparatus of claim 14 wherein said drill comprises a cylindrical shaft having a proximal end adapted for engagement with drill drive means, and a distal end including at least two cutting surfaces adapted to form a first substantially conical wall at the bottom of said hole, and wherein said first end of said first portion of said anchor assembly defines a substantially conical wall adapted to mate with the first conical wall at the bottom of said hole.

16. The apparatus of claim 2 wherein:
there are two barbs;
said attachment means comprises a bore extending through said second portion of said anchor assembly and a cord-like connecting member threadingly engaging said bore, said bore having an axis located in a plane containing said first longitudinal axis and a diameter of each of said barbs measured on said second end of said first portion of said anchor assembly; and
said shaft further includes at least one channel in said exterior surface, said channel having a cross-section sized to contain the cross-section of said cord-like member, and extending proximally substantially parallel to said second longitudinal axis from the base of said bore in said distal end of said shaft a predetermined distance at least as great as the intended depth of insertion of said second portion of said body into said hole, whereby said cord-like connecting member may be contained within the cross-section of said shaft to reduce the required cross-section of said hole.

17. The apparatus of claim 16 wherein said bore is formed in said second portion so as to provide a smoothly contoured suture-bearing surface in said second portion, about which said suture can be slid after said anchor assembly has been deployed in bone.

18. A method of attaching an object to a workpiece comprising:
(a) providing:
(1) means for forming a hole in said workpiece;
(2) an anchor assembly comprising a body and at least two barbs;
said body having a longitudinal axis, a first portion having a first end and a second end and a first maximum cross-section transverse to said longitudinal axis, a second portion centered on said longitudinal axis having a first end and a second end and a second cross-section transverse to said longitudinal axis smaller than said maximum transverse cross-section of said first portion, and a middle portion having a first end and a second end, said second end of said first portion being joined to said first end of said middle portion, and said first end of said second portion being joined to said second end of said middle portion,
said middle portion defining at least two equally-circumferentially-spaced channels extending inwardly from an axial projection of the periphery of said first maximum transverse cross-section of said first portion to a base adjacent said longitudinal axis, and said channels extending longitudinally between said second end of said first portion and said second end of said middle portion, said channels being separated by longitudinal walls extending radially of said longitudinal axis to an outer surface located on an axial projection of the periphery of said first maximum transverse cross-section,
said middle portion defining at least two axial grooves extending from said second end of said middle portion towards said first end of said middle portion;
one of said barbs extending axially and radially outwardly from said second end of said first portion adjacent the base of each said channel to an outer end located radially outwardly of said axial projection of said first maximum transverse cross-section of said first portion, each said barb being curved in its normal unrestrained state but capable of being elastically deformed into a substantially straight configuration with its outer end located radially within said axial projection of said first maximum transverse cross-section of said first portion; and
attachment means associated with said second portion for connecting an object to said anchor assembly; and
(3) an insertion tool for deploying said anchor assembly in said hole in said workpiece, said tool comprising an elongate shaft having an exterior surface, a second longitudinal axis, a proximal end, a distal end, a cross-section transverse to said second longitudinal axis substantially the same as said first maximum cross-section of said first portion of said anchor assembly, a bore having a cross-section transverse to said second longitudinal axis substantially the same as said second cross-section of said second portion of said anchor assembly and extending centrally into said distal end of said shaft, said bore being adapted to slidably receive said second portion of said anchor assembly and defining at least two equally-circumferentially-spaced slots extending between said bore and the exterior surface of said shaft, and at least two projections, each projection having substantially the same cross-section transverse to said second longitudinal axis as said cross-sections transverse to said first longitudinal axis of said grooves formed in said middle portion of said anchor assembly so as to be slidably receivable in one of said grooves;
(b) forming a hole in said workpiece with said drill;
(c) aligning said anchor assembly with said installation tool so that said first longitudinal axis is aligned with said second longitudinal axis, and aligning said projections of said insertion tool with said grooves of said anchor assembly;
(d) slidably engaging said second portion of said anchor assembly with said bore in said distal end of said shaft, and said projections of said insertion tool with said grooves of said anchor assembly;
(e) inserting said first portion of said anchor assembly into said hole;
(f) exerting a pushing force upon said shaft axially so as to urge said anchor assembly into said hole such that said barbs deform axially into said channels, and such that said anchor assembly travels to a selected depth within said hole;
(g) withdrawing said tool from said hole by exerting an axial withdrawing force on said shaft; and
(h) attaching said object to said attachment means.

19. The method of claim 18 wherein step (b) occurs at any point prior to step (e).

20. The method of claim 18 wherein said attachment means comprises a bore extending transversely relative to said first longitudinal axis through said second portion of said anchor assembly, and further including the step of threading one end of a cord-like member through said bore prior to step (e) such that said cord-like member is securely attached to said second portion and at least one end of said cord-like member extends out of said hole after step (f).

21. A method for anchoring a suture within a hole formed in a bone, said method comprising:
  (a) providing:
    (1) a piece of suture having two ends;
    (2) an anchor assembly comprising a body and at least two barbs;
      said body having a longitudinal axis, a first portion having a first end and a second end and a first maximum cross-section transverse to said longitudinal axis, a second portion centered on said longitudinal axis having a first end and a second end and a second cross-section transverse to said longitudinal axis smaller than said maximum transverse cross-section of said first portion, and a middle portion having a first end and a second end, said second end of said first portion being joined to said first end of said middle portion, and said first end of said second portion being joined to said second end of said middle portion,
      said middle portion defining at least two equally-circumferentially-spaced channels extending inwardly from an axial projection of the periphery of said first maximum transverse cross-section of said first portion to a base adjacent said longitudinal axis, and said channels extending longitudinally between said second end of said first portion and said second end of said middle portion, said channels being separated by longitudinal walls extending radially of said longitudinal axis to an outer surface located on an axial projection of the periphery of said first maximum transverse cross-section,
      said middle portion defining at least two axial grooves extending from said second end of said middle portion towards said first end of said middle portion;
      one of said barbs extending axially and radially outwardly from said second end of said first portion adjacent the base of each said channel to an outer end located radially outwardly of said axial projection of said first maximum transverse cross-section of said first portion, each said barb being curved in its normal unrestrained state but capable of being elastically deformed into a substantially straight configuration with its outer end located radially within said axial projection of said first maximum transverse cross-section of said first portion; and
      attachment means comprising a bore extending transversely through said second portion; and
    (3) an insertion tool for deploying said anchor assembly in said hole in said workpiece, said tool comprising an elongate shaft having an exterior surface, a second longitudinal axis, a proximal end, a distal end, a cross-section transverse to said second longitudinal axis substantially the same as said first maximum transverse cross-section of said first portion of said anchor assembly, a bore having a cross-section transverse to said second longitudinal axis substantially the same as said second cross-section of said second portion of said anchor assembly and extending centrally into said distal end of said shaft, said bore being adapted to slidably receive said second portion of said anchor assembly and defining at least two equally-circumferentially-spaced slots extending between said bore and said exterior surface of said shaft, and at least two projections, each projection having substantially the same cross-section transverse to said second longitudinal axis as said cross-sections transverse to said first longitudinal axis of said grooves formed in said middle portion of said anchor assembly so as to be slidably receivable in one of said grooves;
  (b) threading one end of said suture through said bore in said second end of said anchor assembly;
  (c) aligning said anchor assembly with said installation tool so that said first longitudinal axis is aligned with said second longitudinal axis, and aligning said projections of said insertion tool with said grooves of said anchor assembly;
  (d) slidably engaging said second portion of said anchor assembly with said bore in said distal end of said shaft, and said projections of said installation tool with said grooves of said anchor assembly;
  (e) inserting said first portion of said anchor assembly into said hole;
  (f) exerting a pushing force upon said shaft axially so as to urge said anchor assembly into said hole such that said barbs deform axially into said channels, such that said anchor assembly travels to a selected depth within said hole, and such that at least one end of said suture extends from said second portion of said anchor assembly out of said hole; and
  (g) withdrawing said tool from said hole by exerting an axial withdrawing force on said shaft.

22. Apparatus for attaching an object to a workpiece, comprising:
  an anchor comprising a body, at least two barbs and attachment means for connecting said object to said anchor assembly;
  said body having an exterior surface, a longitudinal axis, and a maximum cross-section transverse to said longitudinal axis, and comprising a first portion centered on said longitudinal axis having a distal end and a proximal end, and a second portion centered on said longitudinal axis having a distal end and a proximal end, said proximal end of said first portion being joined to said distal end of said second portion;
  said second portion defining at least two equally-circumferentially-spaced channels, each said channel extending inwardly from said exterior surface of said body to a base located substantially adjacent to said longitudinal axis, and also extending longitudinally from said proximal end of said first portion toward said proximal end of said second portion; and
  one of said barbs extending axially and radially outwardly from said proximal end of said first portion adjacent the base of each said channel to an outer end located radially outwardly of an axial projection of said maximum transverse cross-section of said body, each said barb being curved in its normal unrestrained state but capable of being elastically deformed into a substantially straight configuration so as to be disposed at least partially within the channel associated therewith, such that said outer end of said barb is located substantially radially within said axial projection of said maximum transverse cross-section of said body.

23. The apparatus of claim 22 wherein said barbs are made of nickel titanium alloy.

24. The apparatus of claim 22 wherein said first portion of said body defines at least two bores extending longitudinally from said proximal end of said first portion towards said distal end of said first portion, with one bore adjacent the base of each said channel, and wherein each of said barbs is a piece of wire having a first end and a second end, said first end of each said wire fixedly engaging one of said bores in said first portion.

25. The apparatus of claim 24 wherein the combined longitudinal length of said first portion of said body and said second portion of said body measured parallel to said longitudinal axis is substantially the same as the length of each of said pieces of wire when said pieces of wire are deformed into their substantially straight configuration.

26. The apparatus of claim 22 wherein said attachment means comprises a bore extending through said body substantially adjacent said proximal end of said second portion of said body and substantially transversely to said longitudinal axis.

27. The apparatus of claim 22 wherein said body further comprises a third portion centered on said longitudinal axis having a distal end, a proximal end and a cross-section transverse to said longitudinal axis smaller that said maximum cross-section transverse to said longitudinal axis of said body, said distal end of said third portion being joined to said proximal end of said second portion.

28. The apparatus of claim 22 wherein the exterior surface of said body tapers toward said longitudinal axis as it extends toward said distal end of said first portion.

29. A system for attaching an object to a workpiece, comprising:
(a) an anchor assembly comprising a body, at least two barbs and attachment means for connecting said object to said anchor assembly;
said body having an exterior surface, a longitudinal axis, and a maximum cross-section transverse to said longitudinal axis, and comprising a first portion centered on said longitudinal axis having a distal end and a proximal end, and a proximal portion centered on said longitudinal axis having a distal end and a proximal end, said proximal end of said first portion being joined to said distal end of said said second portion;
said second portion defined at least two equally-circumferentially-spaced channels, each said channel extending inwardly from said exterior surface of said body to a base located substantially adjacent to said longitudinal axis, and also extending longitudinally from said proximal end of said first portion toward said proximal end of said second portion; and
one of said barbs extending axially and radially outwardly from said proximal end of said first portion adjacent the base of each said channel to an outer end located radially outwardly of an axial projection of said maximum transverse cross-section of said body, each said barb being curved in its normal unrestrained state but capable of being elastically deformed into a substantially straight configuration so as to be disposed at least partially within the channel associated therewith, such that outer end of said barb is located substantially radially within said axial projection of said maximum transverse cross-section of said body; and
(b) an insertion tool for deploying said anchor assembly in a hole in said workpiece, said insertion tool comprising an elongate shaft having a longitudinal axis, a distal end and a proximal end, said distal end including engagement means adapted to engage said body.

30. A method for attaching an object to a workpiece, comprising:
providing:
(a) (1) means for forming a hole in said workpiece;
(2) an anchor assembly comprising a body, at least tow barbs and attachment mean for connecting said object to said anchor assembly;
said body having an exterior surface, a longitudinal axis, and a maximum cross-section transverse to said longitudinal axis, and comprising a first portion centered on said longitudinal axis having a distal end and a proximal end, and a second portion centered on said longitudinal axis having a distal end and a proximal end, said proximal end of said first portion being joined to said distal end of said said second portion;
said second portion defining at least two equally-circumferentially-spaced channels, each said channel extending inwardly from said exterior surface of said body to a base located substantially adjacent to said longitudinal axis, and also extending longitudinally from said proximal end of said first portion toward said proximal end of said second portion; and
one of said barbs extending axially and radially outwardly from said proximal end of said first portion adjacent the base of each said channel to an outer end located radially outwardly of an axial projection of said maximum transverse cross-section of said body, each said barb being curved in its normal unrestrained state but capable of being elastically deformed into a substantially straight configuration so as to be disposed at least partially within the channel associated therewith, such that said outer end of said barb is located substantially radially within said axial projection of said maximum transverse cross-section of said body; and
(3) an insertion tool for deploying said anchor assembly in a hole in said workpiece, said insertion tool comprising an elongates haft having a longitudinal axis, a distal end and a proximal end, said distal end including engagement means adapted to engage said body; and
aligning said anchor assembly with said installation tool so that the anchor assembly's longitudinal axis is aligned with the tool's longitudinal axis, and engaging said anchor with said insertion tool engagement means; and
forming a hole in said workpiece with said hole forming means;
(b) inserting said first portion of said anchor assembly into said hole;
(c) exerting an axially directed pushing force upon said shaft of said insertion tool so as to urge said anchor assembly into said hole such that said barbs deform into said channels, and such that said anchor assembly travels to a selected depth within said hole;

(d) withdrawing said insertion tool from said hole by exerting an axially directed withdrawing force on said shaft; and (e) attaching said object to said attachment means.

31. The method of claim 30 wherein said barbs are made of nickel titanium alloy.

32. The method of claim 30 wherein said attachment means comprises a body extending through said body of said anchor assembly transverse to its longitudinal axis, and further including the step of threading one end of a cord-like member through said bore prior to step (b) such that said cord-like member is securely attached to said body and at least one end of said cord-like member extends out of said hole after step (c).

33. The apparatus of claim 32 wherein said bore of said attachment means is formed so as to provide a smoothly contoured bearing surface about which said cord-like member can be slid after said anchor assembly has been deployed in said workpiece.

34. Apparatus for attaching an object to a surface of said workpiece having a hole formed therein, said apparatus comprising:

an anchor comprising a body, at least two barbs and attachment means for attaching said object to said anchor;

said body having a longitudinal axis, a distal end, a proximal end, an exterior surface, and a maximum cross-section transverse to said longitudinal axis no greater than the transverse cross-section of said hole;

at least two equally-circumferentially-spaced longitudinal channels, each said channel extending radially into said body from said exterior surface, and having a distal end disposed toward said distal end of said body and a proximal end disposed toward said proximal end of said body;

one of said barbs extending axially and radially outwardly from said distal end of each said channel to an outer end located radially outwardly of an axial projection of said maximum transverse outwardly of an axial projection of said maximum transverse cross-section of said body, each said barb being curved in its normal unrestrained state but capable of being elastically deformed into a substantially straight configuration so as to be disposed at least partially within the channel associated therewith, such that said outer end of said barb is located substantially radially within said axial projection of said maximum transverse cross-section of said body.

35. Apparatus for attaching an object to a workpiece of the sort having a hole formed therein, said apparatus comprising:

an anchor comprising a body, at least two barbs and attachment means for attaching said object to said anchor;

said body having a longitudinal axis, a distal end, a proximal end, an exterior surface, and a maximum cross-section transverse to said longitudinal axis no greater than the transverse cross-section of said hole in said workpiece;

at least two equally-circumferentially-spaced longitudinal channels, each said channel extending radially into said body from said exterior surface, and having a distal end disposed toward said distal end of said body and a proximal end disposed toward said proximal end of said body;

one of said barbs being rigidly attached to said body; adjacent said distal end of each said channel and being adapted so as to normally extend axially and radially outwardly from said distal end of each said channel to an outer end located radially outwardly of an axial projection of said maximum transverse cross-section of said body, with each said barb being capable of being elastically deformed so as to be disposed at least partially within the channel associated therewith, such that said outer end of said barb is located substantially radially within said axial projection of said maximum transverse cross-section of said body.

36. Apparatus according to claim 35 wherein said barbs are formed out of nickel titanium alloy.

37. Apparatus according to claim 35 wherein said attachment means comprises a bore extending through said body transversely to said longitudinal axis.

* * * * *

UNITED STATES PATENT AND TRADEMARK OFFICE
CERTIFICATE OF CORRECTION

PATENT NO. : 5,207,679
DATED : May 4, 1993
INVENTOR(S) : Lehmann K. Li

It is certified that error appears in the above-indentified patent and that said Letters Patent is hereby corrected as shown below:

Claim 2, column 13, line 17, after the word "workpiece;", a new paragraph should be started before "b)";

Claim 29, column 19, line 67, after the word "that", insert the word -- said --;

Claim 30, column 20, line 14, the word "tow" should be -- two --;

Claim 34, column 21, lines 40-41, after the word "transverse", the words "outwardly of an axial projection of said maximum transverse" should be deleted; and Claim 35, column 22, line 25, the semi-colon (;) after the word "body" should be deleted.

Signed and Sealed this

Fourth Day of April, 1995

Attest:

BRUCE LEHMAN

Attesting Officer

Commissioner of Patents and Trademarks